(12) United States Patent
Wiggenhauser et al.

(10) Patent No.: US 7,252,304 B2
(45) Date of Patent: Aug. 7, 2007

(54) POSITIONING VEHICLE FOR POSITIONING A TEST PROBE

(75) Inventors: Herbert Wiggenhauser, Berlin (DE); Dieter Schaurich, Berlin (DE)

(73) Assignee: BAM, Berlin (DE)

( * ) Notice: Subject to any disclaimer, the term of this patent is extended or adjusted under 35 U.S.C. 154(b) by 149 days.

(21) Appl. No.: 11/067,126

(22) Filed: Feb. 25, 2005

(65) Prior Publication Data

US 2006/0191358 A1    Aug. 31, 2006

(51) Int. Cl.
*G01D 11/00* (2006.01)
(52) U.S. Cl. ........................ 280/769; 73/866.5
(58) Field of Classification Search ........... 280/769; 73/866.5
See application file for complete search history.

(56) References Cited

U.S. PATENT DOCUMENTS

| | | | | |
|---|---|---|---|---|
| 4,315,426 A | * | 2/1982 | Brandon | 73/9 |
| 5,739,442 A | * | 4/1998 | Schweitzer et al. | 73/866.5 |
| 5,819,863 A | * | 10/1998 | Zollinger et al. | 73/866.5 X |
| 5,847,270 A | * | 12/1998 | Nettleton | 73/866.5 X |
| 5,892,360 A | * | 4/1999 | Willer et al. | 324/326 |
| 6,935,201 B2 | * | 8/2005 | Abraham et al. | 73/865.8 |
| 2005/0034544 A1 | * | 2/2005 | Thornhill et al. | 73/866.5 X |
| 2005/0120812 A1 | * | 6/2005 | Edwin et al. | 73/866.5 X |

FOREIGN PATENT DOCUMENTS

| | | | | |
|---|---|---|---|---|
| JP | 03123857 A | * | 5/1991 | 73/866.5 |
| JP | 63111508 A | * | 5/1998 | |

* cited by examiner

*Primary Examiner*—Thomas P. Noland
(74) *Attorney, Agent, or Firm*—Fay Kaplun & Marcin, LLP

(57) ABSTRACT

Described is a method for operating a positioning vehicle for positioning a test probe in defined intervals along a travel line, as well as to a positioning vehicle for carrying out the method. The positioning vehicle contains a traveling vehicle base part with a guide device and with a test probe carrier guided by this guide device in a guide. The guiding has a first reversal point and a second reversal point. The guide device comprises guide means in order on displacing the vehicle base part to guide the test probe carrier in the travel direction up to the first reversal point after it has reached the second reversal point, and in order to lead back the test probe carrier opposite to the travel direction up to the second reversal point after it has reached the first reversal point. In the phase of the return, the test probe carrier relative to the vehicle base part has the negative speed of the vehicle base part. Described is also a device which permits in particular objects having large surfaces to be scanned with little effort.

7 Claims, 3 Drawing Sheets

POSITIONING VEHICLE FOR POSITIONING A TEST PROBE

FIELD OF INVENTION

The invention relates to a method for operating a positioning vehicle for positioning a test probe at defined distances along a travel line, and to a positioning vehicle for carrying out the method.

BACKGROUND INFORMATION

In the building industry it is often necessary to inspect the quality of a building construction. At the same time it may also be useful to inspect the quality of the construction during its phase of being built as well as after completion of the building work. Such an inspection, in particular with tunnels and bridges, is obligatory.

It is known to test building constructions by way of methods which are based on sound. Counted amongst these are the ultrasonic measurement method and the impact echo method. These methods are for example applied for determining the thickness of concrete parts, for localizing pre-stressing cuts and for locating defect locations. Both methods may be used individually and independently, or in combination, for recording readings. The basis of the methods is the examination of the running time and frequency behavior of the longitudinal waves at various measurement points of the object to be examined.

The quality of a building construction is inspected in that readings are recorded at various points of the building construction by way of test probes, which for example are based on the ultrasound method or on the impact echo method. One obtains information as to how the quality of the building construction is to be assessed on the basis of the recorded readings.

However one only obtains the readings for the locations at which a measurement is carried out. With an extensive building construction therefore measurements need to be carried out at many different locations. For this reason it is usual to introduce [modular] grids for the purpose of systemizing the measurement. Readings are recorded by measurements at the individual points of the grid. The measurement effort is reduced by way of this, whilst simultaneously ensuring that the building construction has been inspected in a manner covering its surface.

For inspecting a building construction, a test probe is placed at the locations of the building construction which are characterized by grid, and the readings are recorded at this location.

These measurements may be carried out manually. However the operation of the measurement apparatus changes on account of the fatigue of the personnel, which may considerably compromise the measurement accuracy. Inspections of an extensive area as a rule demand a large number of individual measurements. These then are particularly susceptible to the influences of operation.

In order to automize the measurement method at least partly, it is known to lay rails along a line of grid points, on which a measurement device is guided. The measurement device moves, usually automatically, to the individual grid points which are selected by the guiding of the rails, and records readings at these individual grid points by way of a test probe. In this manner one may automatically record a high number of readings along a line, and operating influences on the part of the personnel are almost completely ruled out.

This type of measurement however entails a considerable expense. Before a measurement may be carried out, firstly the rails must be laid along the line on which one would like to scan (cover in a grid-like manner) the object. The rails must be fixed in order to ensure a secure and exact guiding of the measurement device. Since usually several lines need to be scanned, which for example would be the case with the inspection of a large surface, the rails must be disassembled and re-laid. This procedure may furthermore be repeated quite often.

SUMMARY OF THE INVENTION

The present invention relates to a device which permits a test probe to be positioned at defined distances along a travel line, which is independent of an external mechanical guiding and which may be set to a new travel line with little effort, and a further object of the invention is the provision of a method with which in particular the device according to the invention may be operated.

These objects are achieved by a device and by a method according to the independent claims.

The invention provides a positioning vehicle for positioning a test probe at defined distances along a travel line, containing a traveling vehicle base part with a guide device and with a test probe carrier which is guided in a guide by this guide device, wherein the guide guides the test probe parallel to the travel direction of the vehicle base part, and the guide comprises a first reversal point and a second reversal point, and the guide device comprises guide means in order with a displacement of the vehicle base part, to guide the test probe carrier after it reaches the second reversal point in the travel direction up to the first reversal point, and in order after it reaches the first reversal point to return the test probe carrier back to the second reversal point opposite to the travel direction, wherein in the phase of the return, the test probe carrier relative to the vehicle base part has the negative speed of the vehicle base part. By way of this, a device is provided which permits readings to be recorded along a travel line at defined distances and in a defined manner by way of a test probe accommodated on the test probe carrier, said device requiring no external guide such as by way of rails for example. A new travel line of the positioning vehicle according to the invention may be selected in the simplest case by way of re-placing the positioning vehicle.

According to the invention the vehicle base part is movable. In order to ensure this moving ability, the vehicle base part is preferably equipped with four wheels. In principle another number of wheels is also possible and one may also apply chains or likewise instead of the wheels. It is important that the vehicle base part has a certain stability.

In the simplest case the positioning vehicle is displaced in a manual manner. However as an alternative, the positioning vehicle may also comprise a motor by way of which the positioning vehicle may move on its own. If a motor is used, in a preferred embodiment, the speed of the motor and thus also of the positioning vehicle may be selected.

The test probe carrier serves for receiving a test probe. This for example may be a test probe for an ultrasound measurement, or a test probe for the impact echo measurement. One may likewise also fasten several test probes on the test probe carrier, and the simultaneous attachment of various types of test probes is also possible.

A test probe fastened to the test probe carrier for example is positioned along a travel line of the positioning vehicle at defined distances by way of the positioning vehicle according to the invention. It is to be assumed that the test probe carrier is located at the second reversal point at the beginning of the travel of the positioning vehicle along the travel line. If one then begins to displace the positioning vehicle along the travel line, then the test probe carrier and the test probe connected to the test probe carrier are guided to the first reversal point of the guide by the guide device. In this phase the speed of the test probe carrier, measured relative to the ground on which the positioning vehicle is displaced, is greater than that of the vehicle base part. The test probe carrier with the connected test probe thus hurries ahead of the vehicle base part.

If the test probe carrier reaches the first reversal point lying on the guide, the return phase of the test probe carrier begins. In this second phase, on displacing the positioning vehicle, the test probe carrier with the test probe is led back in the guide to the second reversal point by the guide device. The speed of the test probe carrier relative to the vehicle base part corresponds to the negative speed which the positioning vehicle has relative to the ground on which it is displaced. This means that the test probe carrier in the return phase, thus in the phase in which it is led back from the first reversal point to the second reversal point, is located over a fixed location of the ground on which the positioning vehicle is displaced.

During this return phase in which the test probe carrier and thus also the test probe is located over a fixed position of the ground, it is possible to carry out one or more measurements with the test probe. The time which is available in order to carry out these measurements is fixed by the speed with which the positioning vehicle is displaced as well as by the spatial distance between the first and the second reversal point. If one displaces the positioning vehicle more slowly or if one increases the distance between the two reversal points, then the period of time in which the test probe is located over a fixed location of the ground is extended, by which means time-consuming and more extensive measurements such as e.g. multiple measurements are possible. If the positioning vehicle is displaced more quickly, or the distance between the first and the second reversal point is reduced, then the time duration of the return of the test probe carrier is shortened, by which means the period of time in which measurements may be carried is likewise shortened.

The procedure described above begins from new when the test probe carrier finally reaches the second reversal point again.

One preferred embodiment of the invention envisages the test probe carrier being guided with a constant speed from the second to the first reversal point, thus in the phase in which the test probe carrier leads the vehicle base part. If one furthermore fixes the distance between the first and the second reversal point, then the test probe is positioned at exact constant intervals on displacing the positioning vehicle on a ground along the travel line. One may increase or reduce the constant distance between the individual positions by way of increasing or reducing the distance between the first and the second reversal point. In this manner, if one provides the test probe carrier with a test probe, then it is possible to record readings along a travel line which have a defined interval.

The positioning vehicle according to the invention, apart from the positioning of test probes may also be used for other tasks. For example the test probe carrier may be provided with a marking device in order to provide a surface with markings. Moreover the positioning vehicle may also be used for positioning sensors, just as for positioning actuators or tools. A further possibility of using the positioning vehicle is to record pictures at various points of a grid by way of providing the test probe carrier with a picture recording device.

One advantageous further formation envisages the guide device comprising a first switch and a second switch, and the test probe carrier triggering the first switch at the location of the first reversal point and the test probe carrier triggering the second switch at the location of the second reversal point, and the triggering of the first switch activating the guide means for guiding the measuring probe carrier opposite to the travel direction of the vehicle base part, and the triggering of the second switch activating the guide means for guiding the test probe carrier in the travel direction of the vehicle base part.

With regard to the invention, a micro-switch is preferred. Corresponding guide means are activated when the test probe carrier hits the first or the second micro-switch. The position of the micro-switch thus fixes the spatial interval of the first and of the second reversal point. Alternatively, instead of a micro-switch one may also use a reed switch. Basically other switch types such as e.g. light sensors are possible.

One further advantageous further formation of the invention envisages the guide means comprising a revolving belt, which is arranged parallel to the guide of the test probe carrier, and which given a displacement of the vehicle base part is set into motion by way of mechanical transmission means which transmit a movement of the vehicle base part, and the test probe carrier at the location of the first reversal point, by way of a connection means, connecting to that part of the belt which moves opposite to the travel direction of the vehicle base part, and the test probe carrier at the location of the second reversal point, by way of connection means, connecting to that part of the belt which moves with the travel direction of the vehicle base part.

The revolving belt may be designed in various ways and manners. For example the belt may be a commercially common belt of reinforced fabric. Alternatively however one may also apply a chain. The surface nature of the belt may also vary. According to the invention a belt with a tooth structure which may be set into motion by way of toothed wheels is preferred.

The mechanical transmission means transmit a movement of the vehicle base part which for example is displaced over a base, onto the belt. According to the invention toothed wheels are used as mechanical transmission means but alternatively however the incorporation of belts chains and likewise would be possible. The revolving speed of the belt is directly coupled to the travel speed of the positioning vehicle by way of a purely mechanical transmission of a movement of a positioning vehicle onto the belt. If the positioning vehicle is displaced more quickly, then the peripheral speed of the belt increases, and if the positioning vehicle is displaced more slowly then also the peripheral speed of the belt is accordingly small. This is an essential precondition such that given a displacement of the positioning vehicle, the test probe carrier is positioned at constant intervals, independently of the speed with which the positioning vehicle is displaced. By way of this it becomes possible to displace the positioning vehicle itself in a manual manner without having to compromise the accuracy of the scanning.

The connection means connect the test probe carrier to the revolving belt, by which means a movement of the vehicle base part, for example on displacing the positioning vehicle, is transmitted to the test probe carrier. According to the invention the connection means are designed as a clamping device which clamps onto the belt with a positive fit by way of pressing a part region of the toothed belt against an abutment. However one may also apply connection means which connect with the belt with a non-positive fit.

Alternatively, the guide means which guide the test probe carrier may also contain motors and an electronic control. In this manner it is likewise possible to guide the test probe carrier in the above-described manner on displacing the positioning vehicle. The present invention however consciously emphasizes an almost purely mechanical solution.

One further advantageous further formation of the invention envisages the guide of the test probe carrier comprising two guide rods which guide the test probe carrier.

The stability of the test probe carrier is ensured by using two guide rods. The use of only one guide rod would also be possible, however one would then have to implement design measures in order to ensure a sufficient stability of the test probe carrier. One may also apply rails as an alternative, in which the test probe carrier is guided.

A further possibility of improving the stability of the test probe carrier is to connect the test probe carrier directly to the guide rods, and to mount the guide rods in the vehicle base part in a moveable/displaceable manner.

The length of the guide rods determines the maximal distance of the first and second reversal point. For this reason the guide rods are preferably exchangeable in order to be able to adapt the positioning vehicle to different conditions. If for example one wishes to place a test probe at very large intervals along a travel line by way of the positioning vehicle according to the invention, one would then use correspondingly long guide rods for the positioning vehicle.

One further advantageous further formation of the invention envisages the test probe carrier comprising linear ball bearings by way of which it is mounted on the guide rods.

By way of this it is ensured that the test probe carrier may move on the guide rods without great friction.

A further advantageous further formation of the invention envisages the test probe carrier comprising a lowering device which lowers when the test probe carrier is located at the location of the first reversal point and which lifts when the test probe carrier is located at the second reversal point.

This further formation according to the invention is particularly advantageous if one wishes to use the positioning vehicle for carrying out ultrasound measurements or impact echo measurements. With these measurements it is necessary to create direct contact between the measurement object and the test probe. The lowering device of the positioning vehicle ensures that the test probe has ground contact given any travel (displacement) of the positioning vehicle in the phase of the return of the test probe carrier.

One further advantageous further formation of the invention envisaged the lowering device comprising an air cylinder for the purpose of producing a uniform contact pressure.

Alternatively in place of the air cylinder one may also apply a magnetic lift insert. The use of a spindle for lowering the test probe carrier is just as possible.

In this manner for example a test probe which is fastened on the test probe carrier is pressed onto an object to be examined with a constant pressure. If one scans a base with such a positioning vehicle, then the unevenness of the ground has no influence on the measurement since the contact pressure is always the same.

DETAILED DESCRIPTION OF THE INVENTION

Figure 1:
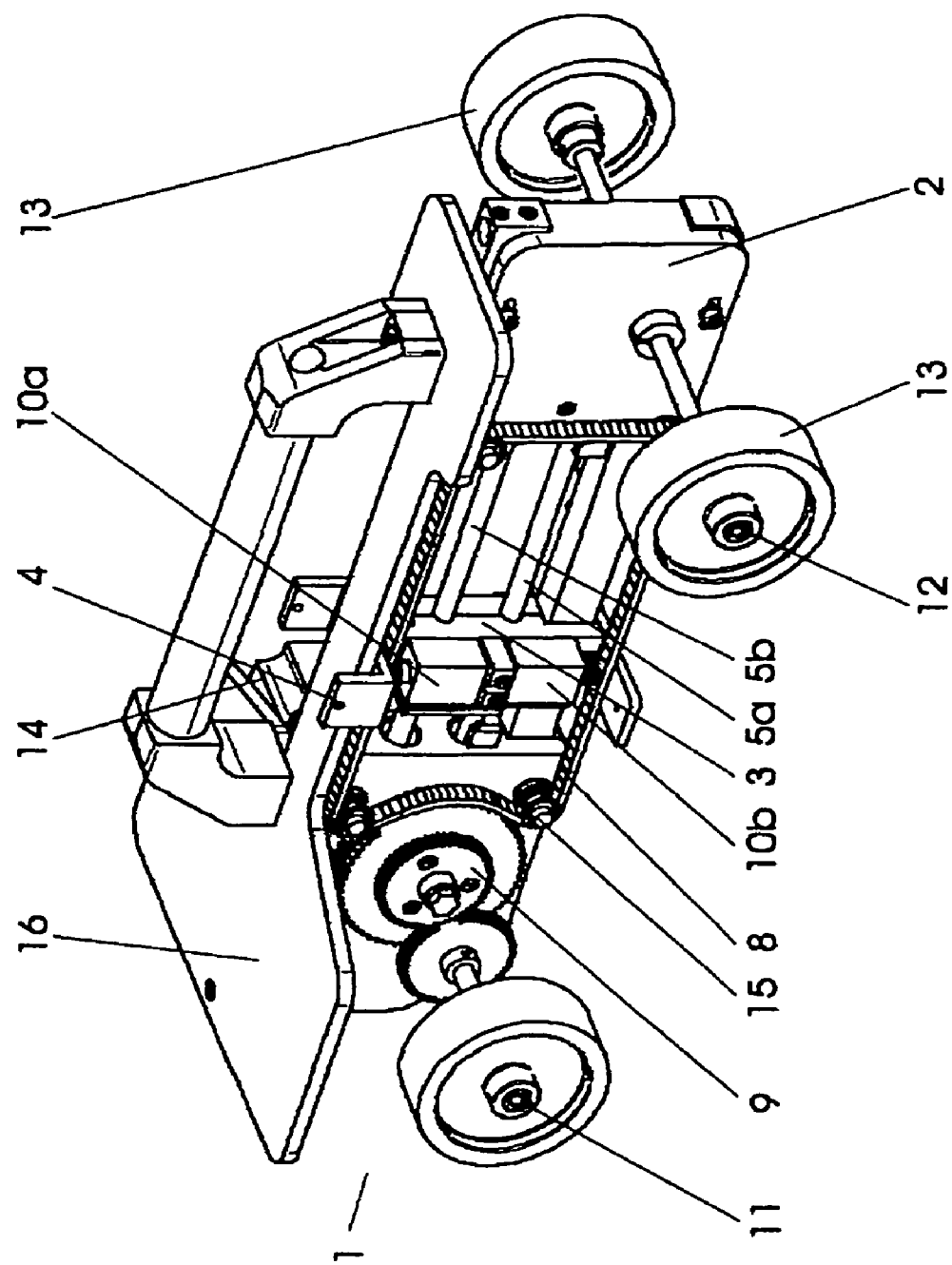
FIG. 1 shows a positioning vehicle according to an exemaplry embodinet of the invention in a transverse section.
Figure 2:
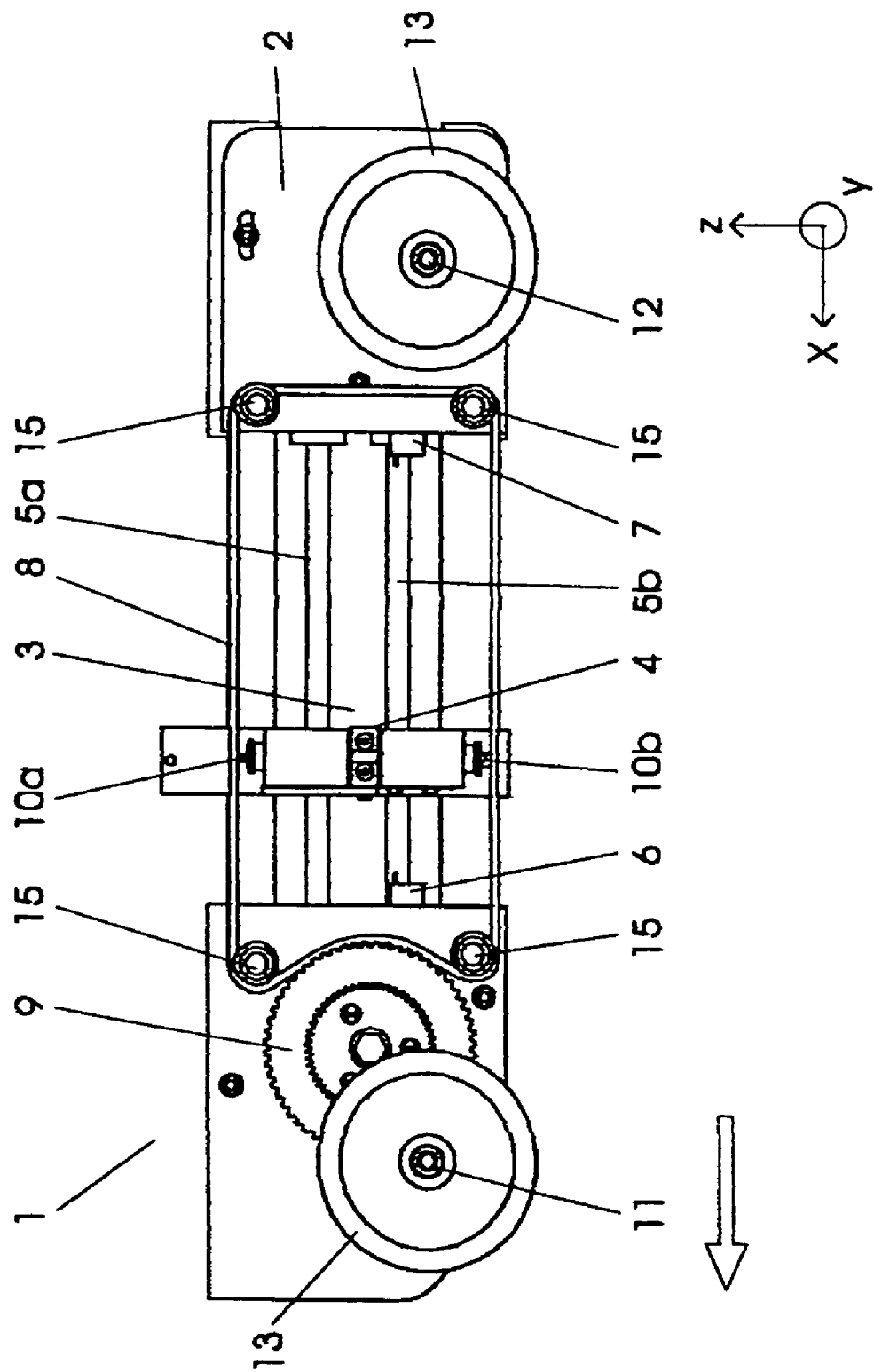
FIG. 2 shows a lateral view of the vechilce.
Figure 3:
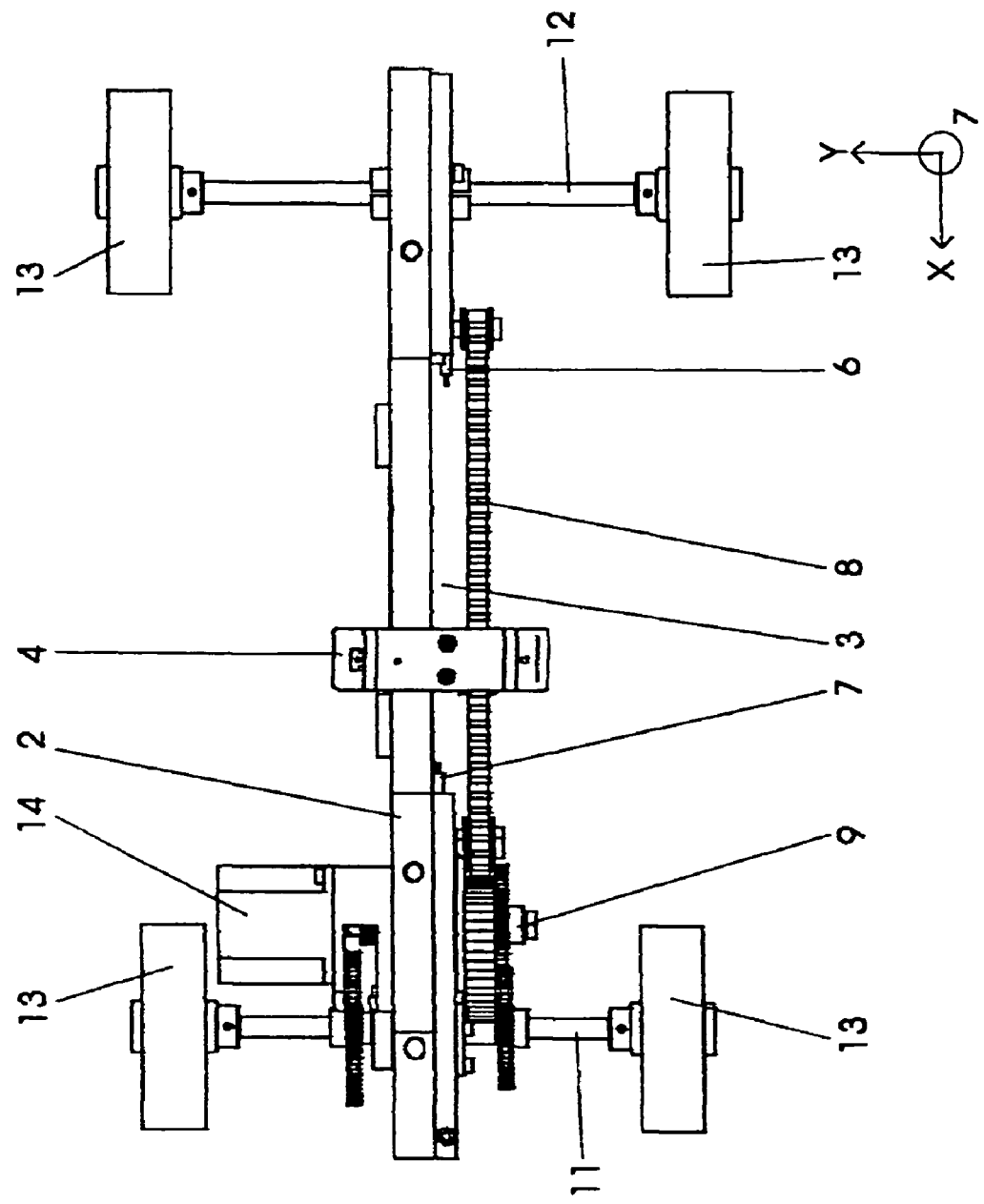
FIG. 3 shows a plan view of the vechicle.

FIGS. 1 to 3 show a positioning vehicle according to the invention in several views. The positioning vehicle 1 contains a traveling vehicle base part 2 with a guide device 3 and with a test probe carrier 4 which is guided in a guide 5 by this guide device 3.

The vehicle base part 2 contains a first axle 11 and a second axle 12 on which in each case two wheels 13 are attached. These axles are arranged parallel to one another and are located at the outer ends of the vehicle base part 2. At the same time the second axle 12 is designed in a particularly wide manner compared to the first axle 11. The arrangements of the axles in the front and rear region of the vehicle base part, as well as the wide design of the second axle serve for providing the positioning vehicle with an adequate stability against tilting. In this embodiment example, the travel line of the positioning vehicle is predefined by the arrangement of the two axles. The positioning vehicle may be displaced along a line. Alternatively however it is also possible to provide the vehicle base part with a steering device with which the axle arrangement may be changed, by which means travel lines different to a line become possible.

Furthermore the vehicle base part 2 comprises a motor 14 which drives the vehicle base part 2 and thus also the positioning vehicle. By way of the motor which is designed as a stepper motor, one may travel the positioning vehicle at constant speeds of a few centimeters per second. By way of switching off the stepper motor 14 it is also possible to manually travel the positioning vehicle.

The guide means 3 guides the test probe carrier 4 in the guide 5 parallel to the travel direction of the vehicle base part 2.

The guide 5 in this embodiment example consists of a first guide rod 5a and of a second guide rod 5b wherein both guide rods are identical and are arranged lying horizontally above one another and are directed parallel to one another. The ends of the guide rods are releasably fastened in the front and the rear region of the vehicle base part 2.

The test probe carrier 4 contains two linear ball bearings by way of which it is mounted on the guide rods 5 in a stable manner.

The guide comprises a first reversal point and a second reversal point. The first reversal point at the same time is fixed by a microswitch 6 and the second reversal point is fixed by a second microswitch 7. Both switches are fastened on the lower guide rod 5a at a defined distance. The switches at the same time are mutually aligned such that these may be triggered by way of a guiding test probe carrier 4 on reaching the first or the second reversal point.

By way of releasing the fastening, the microswitches 6, 7 are displaced on the guide rod 5a. By way of this one may vary the distance between the first and the second reversal point.

The guide device 3 contains a revolving toothed belt 8 which is arranged parallel to the guide 5 of the test probe carrier 4. The belt 8 is tensioned by way of four toothed wheels 15. In each case two toothed wheels are mounted in the front and rear region of the vehicle base part 2. The four toothed wheels are arranged in a common plane, wherein this plane is located in a parallel manner slightly displaced to the plane which is defined by the guide rods 5a and 5b. On this plane the four toothed wheels are arranged such that two toothed wheels are located above the two guide rods 5a and 5b in the Z-direction, and that two toothed wheels 15 are located below the two guide rods 5a in the Z-direction. Furthermore the distance of the toothed wheels 15 in the X-direction is selected such that this distance corresponds to the length of the guide rods 5a and 5b. The toothed wheels are movably mounted so that the belt 8 is movable. A reinforced fabric is used as a belt, which is provided with a tooth structure.

The vehicle base part 2 contains a combination of toothed wheels 9 which transmit a movement of the first axle 11 onto the toothed belt 8. This transmission is created by one of the toothed wheels 9 which engages into the structure of the belt 8. The rotational movement of the first axle 11 on displacing the vehicle base part is geared up/down by way of the combination of gear wheels 9 such that the revolving speed of the belt relative to the vehicle base part corresponds to the travel speed of the vehicle base part 2 and thus of the positioning vehicle 1.

The measurement probe carrier 4 comprises connection means 10 by way of which it may connect to the belt 8. In this embodiment example the connection of the test probe carrier 4 and the belt 8 is created in that the test probe carrier 4 comprises bolts and abutment surfaces, and the bolts press a region of the belt against the abutment surface, by which means a positive-fit connection is created. In this embodiment example a first connection means 10a and a second connection means 10b are provided. The test probe carrier 4 may be connected by way of the first connection means 10a to that section of the belt which moves in the travel direction on displacing the vehicle base part. The test probe carrier 4 may be connected by way of the connection means 10b to that section of the belt 8 which moves opposite to the travel direction of the vehicle base part 2.

The first connection means 10a and the second connection means 10b are activated by the second microswitch 7 and the first microswitch 6. If the test probe carrier 4 reaches the first reversal point, the first microswitch 6 is triggered. The triggering of the first micro-switch, by way of the second connection means 10b leads to the connection of test probe carrier 4 to that section of the belt 8 which moves opposite to the travel direction of the vehicle base part. If the test probe carrier 4 reaches the second reversal point, then the second switch 7 is triggered. The triggering of the second switch 7, by way of the connection means 10a leads to the connection of the test probe carrier to that section of the belt 8 which moves in the travel direction of the vehicle base part. In both procedures, on activation of one of the two connection means, the other connection means is deactivated in order to prevent a blocking of the guide device.

The measurement probe carrier 4 comprises a lowering device which is not explicitly represented in the drawings. For example test probes fastened on the test probe carrier may be lowered by way of the lowering device for the purpose of measurement. The test probe may be pressed by way of the lowering device against an object, usually the ground, on which the positioning vehicle is located.

An air cylinder is integrated in the lowering device. A constant contact pressure is ensured by way of the air cylinder.

By way of an exchange of the guide rods 5a and 5b and of the belt 8 one may convert the positioning vehicle to different lengths. Since the distance with which the positioning vehicle positions the test probe carrier 4 is defined by the distance of the first switch 6 and of the second switch 7, and the maximal distance of the first switch 6 and of the second switch 7 is defined by the length of the guide rods 5a and 5b if this is useful, then by way of an exchange of the guide rods 5a and 5b and of the belt 8 one may enlarge this maximal distance in a practically infinite manner. It may be just as useful to use short guide rods e.g. if the handling ability of the positioning vehicle is very significant.

Furthermore the vehicle base part comprises a receiver device 16. The receiver device 16 has the purpose of accommodating an apparatus, for example an apparatus for operating a test probe. In this embodiment example the receiver device 16 is designed as a plexiglass plate which is arranged over the second axle 12 of the vehicle base part 2.

Such a positioning vehicle according to the invention may be operated according to the following method:

The positioning vehicle 1 is displaced along a selected travel line. During the travel of the positioning vehicle the test probe carrier 4, is guided in the travel direction guided by the guide rods 5a and 5b by way of the belt 8 on account of the connection of the test probe carrier 4 to the belt 8 via the first connection means 10a. The lowering device is not activated during this phase. If the test probe carrier 4 reaches the first reversal point, then the test probe carrier 4 triggers the first switch 6. The triggering of the switch 6, by way of the connection means 10b leads to the test probe carrier 4 being connected to that section of the belt 8 which moves opposite to the travel direction of the positioning vehicle. The connection means 10a is simultaneously deactivated. Furthermore by way of the triggering of the first switch 6 the lowering device is also activated which lowers the test probe carrier. With a further travel of the positioning vehicle, the lowered test probe carrier 4 is led back up to the reversal point by the belt 8. In this phase of the return the test probe carrier 4 during the travel of the positioning vehicle is located exactly over one point. When the test probe carrier 4 finally reaches the second reversal point, then the second switch 7 is triggered. The triggering of the second switch 7 leads to the deactivation of the connection means 10b, to an activation of the connection means 10a, and to a lifting of the test probe carrier 4. This procedure is repeated with a further travel of the positioning vehicle.

The following specific application of the positioning vehicle according to the invention would be conceivable.

The top section of a bridge is to be examined by way of ultrasound. A scanning at distances of 15 cm along various lines is to be provided.

The positioning vehicle according to the invention is accordingly equipped with an ultrasound test probe. The first switch 6 and the second switch 7 are arranged on the guide rod 5a such that they have a distance of 7.5 cm after subtraction of the width of the test probe carrier 4. The positioning vehicle is then positioned at the beginning of the envisaged travel line. The stepper motor is activated by which means the positioning vehicle is moved forwards along the travel line. During the travel of the positioning vehicle 1, the test probe is lowered from the test probe carrier 4 onto the top section of the bridge at distances of 15 cm. One or more ultrasound measurements are carried out in this phase. If the positioning vehicle 1 has traveled the travel line, then it is positioned at the beginning of a further travel line. In this manner the top section of the bridge may be completely scanned.

The invention claimed is:

1. A positioning vehicle for positioning a test probe at predefined intervals along a travel line, comprising:
   a vehicle base part including a guide device; and
   a test probe carrier moved by the guide device relative to the base part parallel to a travel direction of the base part, the guide device defining first and second reversal points, at which a direction of travel of the test probe carrier relative to the base part will reverse and wherein, when moving relative to the base part in a direction opposite the travel direction of the base part, a speed of the test probe carrier relative to the base part is substantially equal to a speed of travel of the base part along the travel line.

2. The device according to claim 1, wherein the guide device includes first and second switches triggered when the test probe carrier reaches the first and second reversal points, respectively.

3. The device according to claim 1, wherein the guide arrangement includes a revolving belt set into motion substantially parallel to the travel direction of the base part by a mechanical transmission arrangement contained in the base part and transmitting a movement of the base part to the belt, wherein the test probe carrier, upon reaching the first reversal point, connects to a first part of the belt moving in a direction opposite to the travel direction of the base part and, upon reaching the second reversal point, connects to a second part of the belt moving in the travel direction of the base part.

4. The device according to claim 1, wherein the guide device includes first and second guide rods which guide the test probe carrier.

5. The device according to claim 4, wherein the test probe is mounted on the guide rods by linear ball bearings.

6. The device according to claim 1, wherein the test probe carrier includes a lowering device which (i) lowers when the test probe carrier reaches the first reversal point and (ii) lifts when the test probe carrier reaches the second reversal point.

7. The device according to claim 6, wherein the lowering device includes an air cylinder which produces a substantially uniform contact pressure.

* * * * *